United States Patent [19]

Ueno et al.

[11] Patent Number: 4,774,237

[45] Date of Patent: Sep. 27, 1988

[54] EXPELLANTS OF PHYTOPATHOGENIC MICROBES

[75] Inventors: Ryuzo Ueno, Nishinomiya; Hiroshi Kita, Takarazuka; Tadashi Nakagawa, Kawanishi, all of Japan

[73] Assignee: Kabushiki Kaisha Ueno Seiyaku Oyo Kenkyujo, Japan

[21] Appl. No.: 11,688

[22] Filed: Feb. 6, 1987

[51] Int. Cl.$^4$ .............................. A01N 43/90
[52] U.S. Cl. ................................. 514/183; 540/457; 540/458; 540/459
[58] Field of Search .............. 540/457, 458, 459; 514/183

[56] References Cited

PUBLICATIONS

Young, P. M. et al., Plant Sci. Lett. 34: 203–209 (1984).
Goldert, M., Ann. Microbiol. (Paris) 124A: 237–241 (1973).
Anand, V. K. et al., Can. J. Bot. 53: 2581–2588 (1975).
Merck Index Nos. 8113–8115, pp. 1187–1188 (1983).

Primary Examiner—Robert T. Bond
Attorney, Agent, or Firm—Saidman, Sterne, Kessler & Goldstein

[57] ABSTRACT

The present invention provides expellants of phytopothogenic microbes comprising rifamycins, which have excellent in prevention of disease in plants with little adverse influence to human body and environments.

4 Claims, No Drawings

EXPELLANTS OF PHYTOPATHOGENIC MICROBES

BACKGROUND OF THE INVENTION

The present invention relates to expellants of phytopathogenic microbes.

Previously, organic mercury, organic arsenic or organic chloride pesticide has been used as the expellant of phyto-pathogenic microbes, but since these pesticides remain in the applied plants for long periods and so when they are ingested as foods the pesticides might reveal chronic toxicity; they also may influence maliciously on the environment.

The compounds having the following general formula:

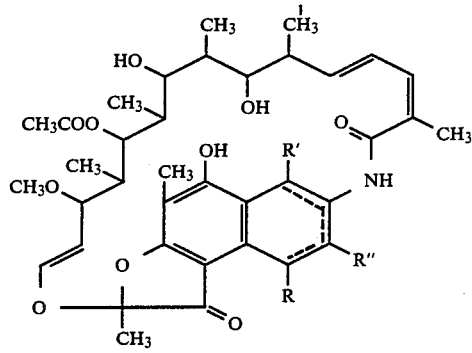

themselves are known as Rifamycins, which have an antibiotic activity (e.g. P. Sensi et al, *Antimicrob. Ag. Chemoth.*, 699 (1966); M. T. Timbal, *Antib. Ann.* 1959–1960, 271 (1960); P. Sensi et al., *Il Farmaco, Ed. Sci.*, 15, 228, 235 (1960); P. Sensi et al., *Experientia*, 16, 412 (1960); and M. T. Timbal et al., *Il Farmaco, Ed. Sci.*, 16, 181 (1961)). However, it has not been known that the compounds have excellent expellant effects on phytopathogenic microbes.

SUMMARY OF THE INVENTION

The present invention provides expellants of phytopathogenic microbes comprising compounds represented by the following general formula:

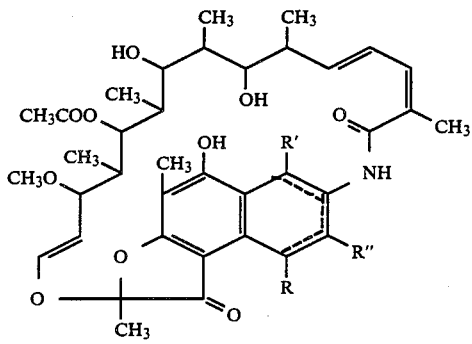

These compounds have excellent expellant effects on phytopathogenic microbes with little adverse effect on human body and environments.

DETAILED DESCRIPTION OF THE INVENTION

The present invention relates to expellants of phytopathogenic microbes essentially comprising compounds having following general formula:

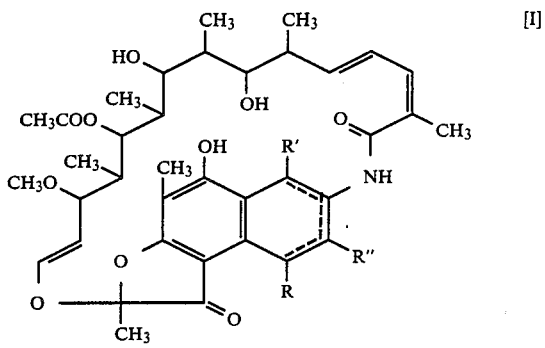

wherein R is hydroxyl, oxo, carboxymethoxyl or (1,3-dioxoran-4-on)-2-yl group, R' is hydroxyl or oxo grop and R" is formyl or (4-methyl-1-piperazinyl) iminomethyl group.

The compounds with the general structure (I) are the antibiotics produced by *Streptomyces mediterranei* and are a mixture of the five components, A, B, C, D, and E, or more. Among them, the compound A has particularly low toxicity.

Compound (A)

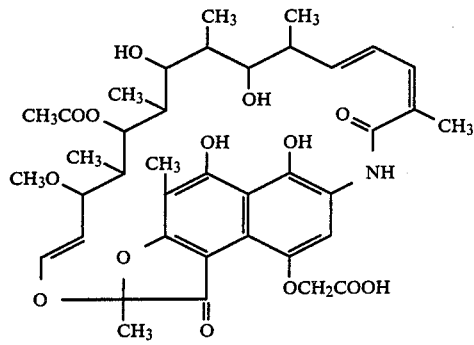

and various derivatives have been obtained from this compound by semi-synthetic technique.

In this invention, following compounds may also be representatives of the compounds with the general structure (I), but they do not limit the invention.

Compound (B)

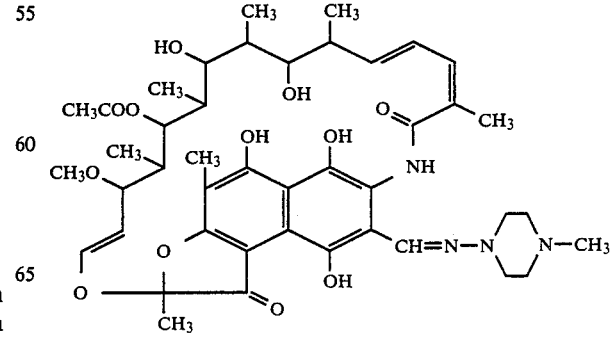

Compound (C)

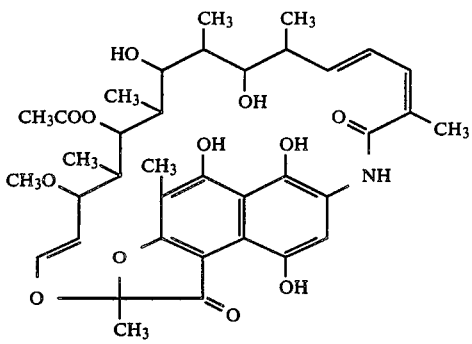

Compound (D)

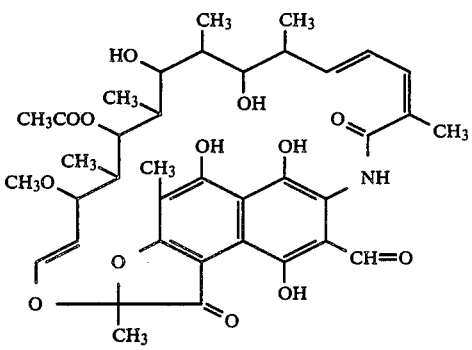

Compound (E)

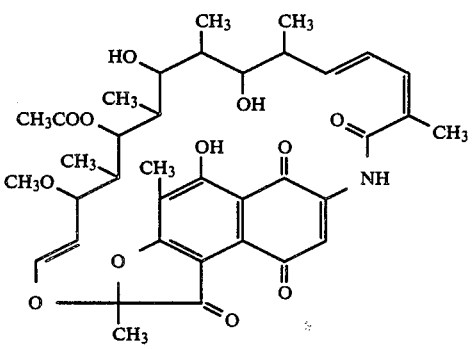

Compound (F)

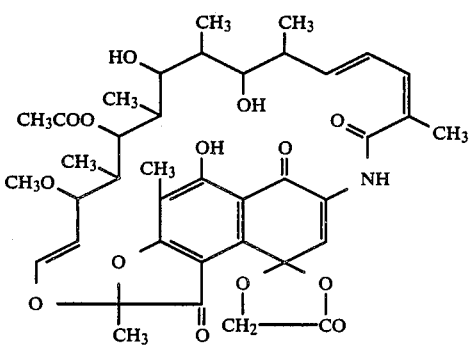

Of these compounds, compounds (B) and (C) are particularly effective.

In application of the expellants by this invention, a single or plural species of the compounds with the general structure (I) may be used as they are, but in many cases they are used in such a type of formulation ordinarily practiced for pesticides as dust, granule, wettable powder or solution. Either of solid or liquid carrier may be employed in formulation, and specific carriers are not necessary. For fitting to the state of infected plants and for potentiating effects, previously known pesticides, insecticides, ascaricides, regulators of plant growth, surfactants, fertilizers or other agents may be mixed with the present expellants.

When the compounds with the general structure (I) are used as solution, the adequate concentrations are 50–2000 ppm, and then used as dust they are desirably contained in the rate of 0.1–3.0%. It is advised to apply the compounds (I) in the rate of 10–1000 g per 10 ares.

The expellants of phytopathogenic microbes according to the present invention are applicable to various kinds of microbes, especially effective to Pseudomonas (*P. mori, P. lachrymans, P. tabaci, P. solanacearum* etc.); Xanthomonas (*X. campestris pv. citri, X. campestris pv. pruni, X. campestris pv., X. oryzae* etc.); Agrobacterium (*A. tumefaciens* etc.); Erwinia (*E. carotovora* etc.); and Corynebacterium (*C. michiganense* etc.).

Examples of plant disease caused by the above bacteria are as follows:

*Pseudomonas mori:* Bacterial blight of Mulberry;

*Pseudomonas lachrymans:* Bacterial spot of Cucumber, Angular leaf spot of Melons, Bacterial wilt of Watermelon, Angular leaf spot of Pumpkin;

*Pseudomonas tabaci:* Wild fire of Tobacco;

*Pseudomonas solanacearum;* Bacterial wilt of Tomato, Eggplant, Sweet pepper, Turnip and Sunflower;

*Xanthomonas (campestris pv.) citri.:* Canker of citrus;

*Xanthomonas (campestris pv.) pruni:* Bacterial shot hole of Peaches, Black spot of Plums, Bacterial shot hole of Apricot;

*Xanthomonas oryzae:* Bacterial leaf blight of Rice;

*Corynebacterium michiganese:* Bacterial canker of Tomato;

*Erwinia carotovora:* Bacterial soft rot of melon, Turnip, Onion, Welsh onion, Lettuce and Carrot, and Bacterial rot of Ginger; and

*Agrobacterium tumefaciens:* Crown gall of Carrot, Sugar beet, Tea, Hop, Citrus, Apple, Pears, Quince, Peaches, Plums, Apricot, Mume, Cherries, Grapes, Persimmons, Chestnuts, Walnuts, Loquat, Fig, Currants and Gooseberries, Blambles, Mango, Papaya, Olive and Passion fruit.

The present invention is illustrated by the following Examples and Experiments.

Following are some examples of the present invention. It is noticed that the content of the major ingredients and the kinds and contents of adjuvant agent shown in these examples do not limit the invention.

EXAMPLE 1 (dusts)

| | |
|---|---|
| Compound (B) | 1% |
| Talc | 99% |

These ingredients are mixed homogeneously and pulverized. In application, the mixture is dusted over plants as it is.

EXAMPLE 2 (granule)

| Compound (C) | 3% |
|---|---|
| Carboxymethylcellulose | 3% |
| Diatomaceous earth | 94% |

These are kneaded thoroughly and molded, and applied around plant roots.

EXAMPLE 3 (wettable powder)

| Compound (B) | 5% |
|---|---|
| Polyoxyethylenealkyl arylether | 20% |
| Diatomaceous earth | 75% |

These are mixed homogeneously and finely pulverized. At use, the powder is diluted with water and sprayed over plants.

Following are experiments regarding the bactericidal effect of the expellants of the present invention.

Experiment 1

(Minimum inhibitory concentration on various phytopathogenic bacteria)

The phytopathogenic bacteria, as shown in Table 1, were used as test organisms and the minimum inhibitory concentration was examined by the dilution method. Thus, compounds (B) and (C) were dissolved to definite concentrations in the YPG broth, and test bacteria were inoculated and incubated at 30° C. for 16 hours (except the *Xanthomonas campestris pv. oryzae* and that the *Corynebacterium michiganense* which are incubated for 24 hours). The minimum inhibitory concentration (ppm) was obtained by estimating turbidity of the broth. The results are shown in Table 1.

TABLE 1

| Test bacteria | Minimum inhibitory concentration (ppm) | |
|---|---|---|
| | Compound (B) | Compound (C) |
| *Pseudomonas mori* (bacterial blight) | 25 | 50 |
| *P. lachrymans* (angular leaf spot, cucumber) | 25 | 50 |
| *P. tabaci* (wildfire) | 25 | 50 |
| *P. solanacerum* (bacterial wilt) | 1.56 | 0.39 |
| *Xanthomonas campestris pv. citri* (canker, citrus fruit) | 0.39 | 0.10 |
| *X. capestris pv. pruni* (bacterial shot hole, peach) | 0.39 | 0.05 |
| *X. campestris* (block rot) | 0.39 | 0.05 |
| *X. oryzae* (bacterial leaf blight, rice) | 0.05 | 0.05 |
| *Corynebacterium michiganense* (bacterial canker, tomato) | <0.0032 | <0.0032 |
| *Erwinia carotovora* (bacterial soft rot, chinese cabbage) | 25 | 6.25 |
| *Agrobacterium tumefaciens* (crown gall) | 3.13 | 0.78 |

Experiment 2

(Evaluation of activity against the Bacterial leaf blight of rice)

Rice plants (variety: KINMAZE) grown in nursery pot to the two-leaves stage were sprayed by the test expellant solutions, prepared by dissolving 0.5 g of Compound (B) in 10 ml of dimethylsulfoxide and diluted to appropriate concentrations with water and adding 0.01% of Tween 20 (polyoxyethylenesorbitan monolaurate) to the mixture, with the use of a glass sprayer in a dose of 30 ml per 3 pots. After air-drying, the *Xanthomonas camestris pv. oryzae* incubated for 48 hours in the Wakimoto medium was sprayed over the plants and after keeping for 2 days in a moist chamber at 25° C., the plants were allowed to grow in a glass green house at 22°–32° C. Fourteen days after the spraying of the pathogenic bacteria, the disease index in the second leaf was examined and the inhibitory percent of infection and inhibitory percent of lesion development were calculated from the following formula:

$$\text{Infection-preventing (\%)} = \frac{\text{diseased leaves (\%) in the control group} - \text{diseased leaves (\%) in the treated group}}{\text{diseased leaves (\%) in the control group}} \times 100$$

$$\text{Inhibitory percent of lesion development (\%)} = \frac{\text{disease index in the control group} - \text{disease index in the treated group}}{\text{disease index in the control group}} \times 100$$

The results are given in Table 2.

For the sake of comparison, results of the similar tests with Sankel wettable powder, a product of Yashima Chemical Industry Co., are also shown in the Table 2.

TABLE 2

| Test agents and concentration | Diseased leaves (%) | Infection-preventing rate (%) | Disease index | Inhibition percent of lesion development (%) |
|---|---|---|---|---|
| Compound (B) 1000 ppm | 52.9 | 27.7 | 48.9 | 14.8 |
| Compound (B) 500 ppm | 58.9 | 19.6 | 51.9 | 9.6 |
| Sankel wettable powder (65%) + 400 1625 ppm | 52.0 | 29.0 | 51.5 | 10.3 |
| Water | 73.2 | — | 57.4 | — |

Experiment 3

(Evaluation of activity against the canker of citrus)

Seedlings of natsukan orange, sown in 1977, were cultured in clay pot, 9–15 cm in diameter, and pruned one month before the test. Over the fresh leaves about 15 days after germination, the test expellant similar to that used in Experiment 1, except only Compound (C) was sprayed by using a glass sprayer in a rate of about 30 ml per pot. After air-drying the *Xanthomonas campestris pv. citri* incubated for 48 hours in a potato sucrose agar medium and sprayed over the plants. They were then kept for 30 hours at 25° C. in a moist chamber and then at 22°–30° C. in a glass green house. Twenty days after the spraying of bacteria, number of lesion per a leaf was counted and the protective value was calculated from the following formula. The results are shown in Table 3. For the purpose of comparison, similar test was conducted with market-available Kosaid wettable powder, purchased from Hokko Chemical Industry Co.

$$\text{Protective value} = \frac{\text{Number of lesions in the control group} - \text{Number of lesions in the treated group}}{\text{Number of lesions in the control group}} \times 100$$

TABLE 3

| Test agents and concentration | Average number of lesion | Protective value |
| --- | --- | --- |
| Compound (C) 1000 ppm | 6.2 | 59.0 |
| Compound (C) 500 ppm | 6.9 | 55.1 |
| Compound (C) 250 ppm | 7.6 | 49.4 |
| Kosaid wettable powder (83%) 415 ppm | 7.0 | 54.8 |
| Water | 15.4 | — |

Experiment 4

(Evaluation of activity against the bacteria leaf blight of rice)

To rice plants (variety: KINMAZE), cultured in nursery pot to the 5-leaves stage, was applied the test solutions prepared by dissolving Compound (C) in 1/100M phosphate buffer (pH 7.8) to definite concentrations and adding 0.01% of Tween 20 (polyoxyethylenesorbitan monolaurate) with the use of a glass sprayer in a rate of 30 ml per 3 pots. After air-drying, the Xanthomonas campestris pv. oryzae, incubated in the Wakimoto medium for 48 hours, was suspended in sterilyzed, physiological saline solution in a concentration of $10^9$ cells/ml and inoculated into the vein nearest to the main vein by injuring rice leaves with needles which were provided with the X. oryzae suspended-physiological saline solution. After inoculation the plants were kept for 24 hours at 25° C. in a moist chamber and in a glass green house for allowing to grow. Two weeks after the bacterial inoculation, existence of blight on the fifth leaves and if any the length of the lesion were estimated, and the inhibitory percent of lesion was calculated from the following formula:

$$\text{Inhibitory percent of lesion} = \frac{\text{Average length of lesions in the control group} - \text{Average length of lesions in the treated group}}{\text{Average length of lesions in the control group}} \times 100$$

For the purpose of comparison, Sankel wettable powder (Yashima Chemical Industry Co.) and Phenazine wettable powder (Nippon Noyaku Co.) were subjected to Similar test. The results are shown in Table 4.

TABLE 4

| Test agents and concentration | diseased leaves (%) | Average length of lesions (cm) | Inhibitory percent of lesion (%) |
| --- | --- | --- | --- |
| Compound (C) 1000 ppm | 60.0 | 3.5 | 78.3 |
| Compound (C) 500 ppm | 96.2 | 6.6 | 59.0 |
| Compound (C) 250 ppm | 97.1 | 6.4 | 60.2 |
| Compound (C) 125 ppm | 93.8 | 4.9 | 69.6 |
| Sankel wettable powder 1625 ppm | 76.9 | 5.0 | 68.9 |
| Phenazine wettable powder 200 ppm | 100.0 | 14.1 | 12.4 |
| 1/100 M phosphate buffer | 100.0 | 14.4 | 10.6 |
| Water | 100.0 | 16.1 | — |

Experiment 5

Navel orange (variety: Shirayanagi) which is sensitive to bacterial canker of citrus fruit was cultured in clay pots of 9–15 cm size. Compound (B), Kosaid wettable powder (Sankyo Co.) and streptomycin wettable powder (Taito-Pfizer Co.) were diluted to appropriate concentrations and by using a glass sprayer they were sprayed over leaves of the orange developed in spring in a rate of 30 ml per pot. After air-drying, the plants were kept in a glass green house for 24 hours. The Xanthomonas campestris pv. citri, isolated from the diseased leaves of the navel orange, was incubated at 27° C. for 24 hours in the Wakimoto medium and suspended in sterilyzed physiological saline solution in a concentration of $10^4$ cells/ml. The bacterial suspension was used for inoculating the bacteria to the leaves of navel orange developed in spring which had been held for 24 hours after the expellant was sprayed, by using a multi-needle scratch-inoculation method. The plants were placed in a warm room at 25° C. for 30 hours and then transferred to a glass green house. Twenty days after the bacterial inoculation, number of lesions per a leaf was counted and the protective value was calculated from the following formula;

$$\text{Protective value} = \frac{\text{Number of lesions in the control group} - \text{Number of lesions in the treated group}}{\text{Number of lesions in the control group}} \times 100$$

The results are shown in Table 5.

TABLE 5

| Test agents and concentration | Average number of lesion per leaf | Protective value (%) |
| --- | --- | --- |
| Compound (B) 1000 ppm | 2.0 | 89.1 |
| Compound (B) 500 ppm | 4.5 | 75.4 |
| Compound (B) 250 ppm | 6.8 | 62.8 |
| Compound (B) 125 ppm | 10.2 | 44.3 |
| Kosaid wettable powder 415 ppm | 8.1 | 55.7 |
| Streptomycin wettable powder 200 ppm | 15.7 | 14.2 |
| Water | 18.3 | — |

Experiment 6

(Evaluation of activity against the bacterial leaf spot of peach)

Five new treetops of 4 year-old seedlings were used in one group, and 5 topside-leaves, 1 just before development and 4 developed, of each seedling were used for testing. The Xanthomonas pv. pruni was incubated for 24 hours in NBA (Nutrient Broth Agar). The bacteria was compulsorly inoculated into 8 sites per a leaf, or total 200 sites per group by the gun press method, and the plants were then left under natural conditions. Compound (B) or (C) was dissolved in 0.01M phosphate buffer, pH 7.0, and sprayed over the plants 1 hour before (for protective value) or 1 hour after (for curative value) the bacterial inoculation, and 10 days' later outbreak of disease was examined to estimate the protective and curative values. The results are shown in Table 6.

TABLE 6

| Agents and concentration | Size of inoculum | | | |
|---|---|---|---|---|
| | $10^{5-6}$/ml | | $10^{3-4}$/ml | |
| | Protective value | Curative value | Protective value | Curative value |
| Compound (C) 200 ppm | 5.6 | 16.7 | 10.3 | 31.7 |
| Compound (B) 200 ppm | 6.0 | 46.3 | 5.0 | 51.6 |
| Streptomycin 200 ppm | 5.4 | 22.6 | 1.2 | 13.0 |

Protective value = $\frac{a - b}{a} \times 100$

Curative value = $\frac{a - c}{a} \times 100$

Experiment 7
(Evaluation of activity against the bacterial spot of cucumber)

Three seedlings of cucumber (variety: Green Tokiwa), grown in a plastic pot of 10.5 cm size to the 2.5-leaves stage that is, when 3 leaves had developed in glass room, were used for the test. Expellants were applied by spraying and irrigation. Compound (B) or (C) was dissolved in 1/100M phosphate buffer, sprayed in a rate of 50 ml per pot, and then air-dried. After that, the pseudomonas lachrymans was inoculated on the test plants. Irrigation was carried out by applying 100 ml of the expellant solution per pot around the root, leaving for 24 hours for allowing to absorb the solution and placing in a glass room until the day of inoculation.

The test bacteria was incubated for 3 days in the Wakimoto medium, adjusted to a concentration of $10^8$ cell/ml and inoculated to both sides of cucumber leaves by spraying. A week after the inoculation the percentage of lesion area in the first and second leaves was estimated. The results are shown in Table 7 and 8.

TABLE 7

| | (Spraying) | | | | | |
|---|---|---|---|---|---|---|
| | Percentage of lesion area | | | | | |
| Test agents and concentration | Diseased leaves (%) | Primary leaves (%) | Second leaves (%) | Average (%) | Disease-preventive rate (%) | Phytotoxity |
| Compound (C) 1000 ppm | 57.2 | 7.2 | 2.7 | 5.0 | 67.9 | — |
| Compound (C) 500 ppm | 73.6 | 9.0 | 3.5 | 6.3 | 59.6 | — |
| Compound (C) 250 ppm | 93.8 | 13.2 | 10.4 | 11.8 | 24.4 | — |
| Compound (B) 1000 ppm | 72.2 | 5.6 | 5.0 | 5.3 | 66.0 | — |
| Compound (B) 500 ppm | 56.3 | 8.1 | 3.8 | 6.0 | 61.5 | — |
| Compound (B) 250 ppm | 94.4 | 11.1 | 11.1 | 11.1 | 28.8 | — |
| Kosaid wettable powder 830 ppm | 84.2 | 11.7 | 6.1 | 8.9 | 42.9 | — |
| Buffer (1/100 M) | 100.0 | 16.3 | 16.3 | 16.3 | 0 | — |
| Water | 100.0 | 18.3 | 12.8 | 15.6 | — | — |

TABLE 8

| | (Irrigation) | | | | | |
|---|---|---|---|---|---|---|
| | Percentage of lesion area | | | | | |
| Test agents and concentration | Diseased leaves (%) | Primary leaves (%) | Second leaves (%) | Average (%) | Disease-preventive rate (%) | Phytotoxity |
| Compound (C) 1000 ppm | 43.2 | 1.6 | 9.2 | 5.4 | 84.4 | — |
| Compound (C) 500 ppm | 61.1 | 3.3 | 11.7 | 7.5 | 78.4 | — |
| Compound (C) 250 ppm | 93.8 | 20.0 | 12.2 | 16.1 | 53.6 | — |
| Compound (B) 1000 ppm | 55.7 | 2.5 | 11.5 | 7.0 | 79.8 | — |
| Compound (B) 500 ppm | 73.5 | 4.7 | 13.2 | 9.0 | 74.1 | — |
| Compound (B) 250 ppm | 94.4 | 18.8 | 23.1 | 31.0 | 10.7 | — |
| Buffer (1/100 M) | 100.0 | 18.8 | 35.0 | 26.9 | 22.5 | — |
| Water | 100.0 | 24.4 | 45.0 | 34.7 | — | — | a: Average number of lesions in control group
b: Average number of lesions when expellants were sprayed 1 hour before the bacterial inoculation
c: Average number of lesions when expellants were sprayed 1 hour after the bacterial inoculation

What is claimed is:
1. A method of controlling a plant disease caused by phytopathogenic microbes selected from the group consisting of Xanthomonas and Corynebacterium, in which a composition essentially containing one or more rifamycins represented by the formula:

[I]

wherein R represents hydroxyl, oxo, carboxymethoxyl or (1,3-dioxoran-4-on)-2-yl group, R' represents hydroxyl or oxo group and R" represents hydrogen atom, formyl or (4-methyl-1-piperazinyl)iminomethyl group is applied to a plant or a soil where a plant is cultured.

2. A method of claim 1, in which the microbes are selected from *Xanthomonas campestris pv. citri, Xanthomonas campestris pv. pruni, Xanthomonas campestris pv., Xanthomonas oryzae,* and *Corynebacterium michiganense.*

3. A method of claim 1, in which the rifamycins are applied to a plant at a concentration of 50–2000 ppm.

4. A method of claim 1, in which the rifamycins are applied to a soil in a ratio of 10–1000 grams per 10 ares.

* * * * *